US008377307B2

(12) United States Patent
Mason

(10) Patent No.: US 8,377,307 B2
(45) Date of Patent: Feb. 19, 2013

(54) PROCESS FOR SORTING DISPERSED COLLOIDAL STRUCTURES

(75) Inventor: Thomas G. Mason, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 580 days.

(21) Appl. No.: 12/576,089

(22) Filed: Oct. 8, 2009

(65) Prior Publication Data
US 2010/0084320 A1    Apr. 8, 2010

Related U.S. Application Data

(60) Provisional application No. 61/103,766, filed on Oct. 8, 2008.

(51) Int. Cl.
*B01D 17/00*    (2006.01)
(52) U.S. Cl. ........ 210/638; 210/600; 210/660; 210/695; 210/767; 210/787; 210/804; 210/806
(58) Field of Classification Search ............... 210/634, 210/638, 639, 650, 651, 695, 702, 734, 748.01, 210/774, 787, 804, 806, 175, 182, 223, 259, 210/321.6, 512.1; 554/8, 12, 20, 54, 175, 554/186, 224; 435/134; 426/430, 439, 601
See application file for complete search history.

(56) References Cited

U.S. PATENT DOCUMENTS

| | | | |
|---|---|---|---|
| 5,543,046 A * | 8/1996 | Van Rijn ..................... 210/490 |
| 6,432,290 B1 * | 8/2002 | Harrison et al. .............. 204/453 |
| 6,497,821 B1 * | 12/2002 | Bellamy et al. ............... 210/651 |
| 7,118,910 B2 * | 10/2006 | Unger et al. .............. 435/288.5 |
| 7,312,085 B2 * | 12/2007 | Chou et al. ..................... 436/43 |
| 7,452,726 B2 * | 11/2008 | Chou et al. ..................... 436/63 |
| 2009/0324904 A1 | 12/2009 | Mason |
| 2010/0021985 A1 | 1/2010 | Mason |
| 2010/0035061 A1 | 2/2010 | Mason et al. |
| 2010/0087352 A1 | 4/2010 | Mason |
| 2010/0322825 A1 * | 12/2010 | Yamakawa et al. ........ 422/82.05 |
| 2011/0163035 A1 * | 7/2011 | Cheng et al. .................. 210/650 |
| 2012/0006760 A1 * | 1/2012 | Toner et al. ................... 210/767 |

FOREIGN PATENT DOCUMENTS
WO    WO-2009064489    5/2009

OTHER PUBLICATIONS

Brown, A.B.D.; Smith, C.G.; Rennie, A.R. Fabricating colloidal particles with photolithography and their interactions at an air-water interface. Phys. Rev. E 2000, 62, 951-960.

Gourley, P.L. and Naviaux, R.K. Optical phenotyping of human mitochondria in a biocavity laser. IEEE Journal of Selected Topics in Quantum Electronics, 2005, 11, 818-826.

(Continued)

*Primary Examiner* — Joseph Drodge
(74) *Attorney, Agent, or Firm* — Venable LLP; Henry J. Daley

(57) ABSTRACT

A method of separating a mixture of discrete structures dispersed in a fluid material includes identifying a target structure and a non-target structure; providing a custom-shaped particle having at least a portion of a surface that is substantially shape-complementary to a portion of a surface of the target structure; introducing the custom-shaped particle into the fluid material; exciting reconfigurations of the custom-shaped particle with respect to the target structure and the non-target structure; binding the custom-shaped particle to the target structure through an attractive interaction to form an aggregate; and isolating the aggregate containing the target structure and the custom-shaped particle from the non-target structure. The custom-shaped particle preferentially binds with the target structure without binding with the non-target structure.

18 Claims, 10 Drawing Sheets

OTHER PUBLICATIONS

Hernandez, C.J.; Mason, T.G. Colloidal alphabet soup: Monodisperse dispersions of shape-designed designed LithoParticles. J. Phys. Chem. C 2007, 111, 4477-4480.

Hernandez, C.J.; Zhao, K.; Mason, T.G. Pillar-deposition particle templating: A high-throughput throughput synthetic route for producing LithoParticles. Soft Materials 2007, 5, 1-11.

Hernandez, C.J.; Zhao, K.; Mason, T.G. Well-deposition particle templating: Rapid mass-production production of LithoParticles without mechanical imprinting. Soft Materials 2007, 5, 13-31.

Higurashi, E.; Ukita, H.; Tanaka, H.; Ohguchi, O. Optically induced rotation of anisotropic micro-objects fabricated by surface micromachining. Appl. Phys. Lett. 1994, 64, 2209-2210.

Mason, T.G. Osmotically driven shape dependent colloidal separations. Phys. Rev. E 2002, 66, 060402/1-4.

Rolland, J.P.; Maynor, B.W.; Euliss, L.E.; Exner, A.E.; Denison, G.M.; DeSimone, J.M. Direct fabrication of monodisperse shape-specific nanobiomaterials through imprinting. J. Am. Chem. Soc. 2005, 127, 10096-10100.

Sullivan, M.; Zhao, K.; Harrison, C.; Austin, R.H.; Megens, M.; Hollingsworth, A.; Russel, W.B.; Cheng, Z.; Mason, T.G.; Chaikin, P.M. Control of colloids with gravity, temperature gradients, and electric fields. J. Phys. Condens. Matter 2003, 15, S11-S18.

Voeltz, G.K. and Prinz, W.A. Sheets, ribbons, and tubules—how organelles get their shape. Nature Reviews, 2007, 8, 258-264.

Zhao, K.; and Mason, T.G, Directing Colloidal Self-Assembly Through Roughness-controlled depletion attractions for directing colloidal self-assembly. Phys. Rev. Lett. 2007, 99, 268301/1-4.

Zhao, K.; and Mason, T.G. Suppressing and enhancing depletion attractions between surfaces roughened by asperities. Phys. Rev. Lett. 2008, 101, 148301/1-4.

\* cited by examiner

➕ = A Chosen Target Structure

▲ = A Non-Target Structure

⬟ = A Non-Target Structure binding non-binding

PROCESS FOR SORTING DISPERSED COLLOIDAL STRUCTURES

CROSS-REFERENCE TO RELATED APPLICATION

This application claims priority to U.S. Provisional Application No. 61/103,766 filed Oct. 8, 2008, the entire contents of which is hereby incorporated by reference.

BACKGROUND

1. Field of Invention

This application relates to processes and systems for sorting structures dispersed in a fluid and more particularly processes and systems for sorting sub-millimeter structures dispersed in a fluid using custom-shaped particles.

2. Discussion of Related Art

The contents of all references, including articles, published patent applications and patents referred to anywhere in this specification are hereby incorporated by reference.

A variety of different approaches using lithography (Madou, M. J. *Fundamentals of microfabrication: The science of miniaturization.* 2nd ed.; CRC Press: Boca Raton, 2002) now exist for designing and making custom-shaped sub-millimeter particles dispersed in a fluid (Hernandez, C. J.; Mason, T. G. Colloidal alphabet soup: Monodisperse dispersions of shape-designed LithoParticles. J. Phys. Chem. C 2007, 111, 4477-4480; Hernandez, C. J.; Zhao, K.; Mason, T. G. Pillar-deposition particle templating: A high-throughput synthetic route for producing LithoParticles. Soft Materials 2007, 5, 1-11; Hernandez, C. J.; Zhao, K.; Mason, T. G. Well-deposition particle templating: Rapid mass-production of LithoParticles without mechanical imprinting. Soft Materials 2007, 5, 13-31; Higurashi, E.; Ukita, H.; Tanaka, H.; Ohguchi, O. Optically induced rotation of anisotropic micro-objects fabricated by surface micromachining. Appl. Phys. Lett. 1994, 64, 2209-2210; Rolland, J. P.; Maynor, B. W.; Euliss, L. E.; Exner, A. E.; Denison, G. M.; DeSimone, J. M. Direct fabrication of monodisperse shape-specific nanobiomaterials through imprinting. J. Am. Chem. Soc. 2005, 127, 10096-10100; Brown, A. B. D.; Smith, C. G.; Rennie, A. R. Fabricating colloidal particles with photolithography and their interactions at an air-water interface. Phys. Rev. E 2000, 62, 951-960; Sullivan, M.; Zhao, K.; Harrison, C.; Austin, R. H.; Megens, M.; Hollingsworth, A.; Russel, W. B.; Cheng, Z.; Mason, T. G.; Chaikin, P. M. Control of colloids with gravity, temperature gradients, and electric fields. J. Phys. Condens. Matter 2003, 15, S11-S18). Shape-designed particles, regardless of the methods of production, will also be referred to as LithoParticles in this specification. Because the shapes of the particles can be specified and designed, these processes for making custom-shaped particles can often be adapted to make desired particle shapes that may have enhanced functionality owing to prespecified geometrical features inherent in their shapes.

The certain attractive interactions, including those created by depletion attractions, between dispersed particles in a liquid can be anisotropic and can depend on the relative orientations of the particles (Mason, T. G. Osmotically driven shape dependent colloidal separations. Phys. Rev. E 2002, 66, 060402/1-4). The discotic particles discussed by Mason in this particular article in Phys. Rev. E are not custom-shaped particles produced by any lithographic method; the method of making the particles did not involve an element of prescriptive design of their shapes. By contrast, controlled surface roughness on colloidal particles can be used to further control the strength of attractive interactions between custom-shaped particles that have been produced lithographically (Zhao, K.; and Mason, T. G. Roughness-controlled depletion attractions for directing colloidal self-assembly. Phys. Rev. Lett. 2007, 99, 268301/1-4; Zhao, K.; and Mason, T. G. Suppressing and enhancing depletion attractions between surfaces roughened by asperities. Phys. Rev. Lett. 2008, 101, 148301/1-4). Although dimer assemblies of certain particle types have been created by design, there is no element of isolation, separation, and sorting in this approach. Thus, the potential exists to design and make custom-shaped particles for interacting with and specifically binding in a form of primitive recognition with a variety of target structures dispersed in a fluid. These target structures could include biological objects, such as cells, organelles, and proteins, as well as non-biological objects, such as synthetic particles. Once bound, the aggregate of a custom shaped particle with a target structure could potentially be isolated, separated, and sorted, typically through the action of an external field or flow. This possibility would be highly useful because the formation of aggregates would occur in a highly parallel process everywhere in a dispersion that would contain both custom-shaped particles and target structures.

It would be therefore highly advantageous to take advantage of shape-specific binding by designing custom-shaped particles that can be induced to bind with one or more specific structures but not to other structures for the purposes of shape-selective recognition, identification, isolation, separation, and sorting. Past approaches in the general area have lacked the combination of custom-designing the lithographic particles for the specific desired shape and to exclude binding with other shapes along with the methods for efficiently extracting the bound objects from the other structures. It is precisely this combination that would provide a highly useful process for isolating, separating, and sorting dispersed sub-millimeter structures.

New methods for making custom-shaped colloidal particles offer unique opportunities for capturing and separating specific molecular, particulate, and cellular species in soft colloidal materials that contain a complex variety of components. An excellent example of a soft colloidal material is normal adult human blood, which can contain a wide variety of proteins, complexes, and cells in an aqueous solution at a well-regulated pH. Among the current challenges in the fields of biomedicine and nanomedicine, it is important to develop methods of efficiently separating different components and cell types in human blood with a high degree of shape and size specificity. Diagnostic methods that rely on detecting very small numbers of abnormal cells in blood are also highly desirable. Beyond detection, shape-selective separation of small numbers of abnormal cells in a viable state that would permit further study would be a major breakthrough.

Normal human peripheral blood can contain a wide variety of cell types, including band neutrophils, segmented neutrophils, basophils, eosinophils, erythrocytes (red blood cells), lymphocytes (white blood cells), monocytes, and platelets. Of these main categories of cell types, numerous sub-categories and refinements of these cell types also exist. Additional diversity in cells types and shapes can be present for human blood in diseased states, including for various disease types such as anemias and cancers. Normal human red blood cells are disk-like, readily deformable, and have biconcave dimples, and they are quite uniform in shape and size, having a low polydispersity. The size and shape of the red blood cells can even change to some degree depending upon the age of the cell and its biological history. By contrast, other cell types in human blood, such as lymphocytes, have shapes and sizes that are not disk-like. In addition to shape and size, the compositions and effective roughness of the surfaces of different cell types can likewise be potentially used to distinguish one cell type from another. (See also, U.S. application Ser. No. 12/377,773 filed Feb. 17, 2009 as a national stage application of PCT/US07/18365, titled "Customized Lithographic Particles"; U.S. application Ser. No. 12/563,907 titled "Mechanical Process for Creating Particles in a Fluid" filed Sep. 21, 2009 as a CIP of PCT/US08/03679; U.S. application Ser. No. 12/575,920 titled "Process for Creating Shape-Designed Particles in a fluid" filed Oct. 8, 2009; U.S. application Ser. No. 12/524,946 filed Jul. 29, 2009 as a national stage application of PCT/US08/01443, titled "Massively Parallel Assembly of Composite Structures using Depletion Attraction"; and PCT/US08/12832 titled "Process for Directing Assemblies of Particulate Dispersions Using Surface Roughness," all by the same assignee as the current application and the entire contents of each of which are hereby incorporated by reference.) There thus remains a need for improved methods and systems for sorting sub-millimeter particles dispersed in a fluid.

SUMMARY

A method of separating a mixture of discrete structures dispersed in a fluid material according to an embodiment of the current invention includes identifying a target structure and a non-target structure; providing a custom-shaped particle having at least a portion of a surface that is substantially shape-complementary to a portion of a surface of the target structure; introducing the custom-shaped particle into the fluid material; exciting reconfigurations of the custom-shaped particle with respect to the target structure and the non-target structure; binding the custom-shaped particle to the target structure through an attractive interaction to form an aggregate; and isolating the aggregate containing the target structure and the custom-shaped particle from the non-target structure. The custom-shaped particle preferentially binds with the target structure without binding with the non-target structure.

A system for separating a mixture of discrete structures dispersed in a fluid material has a particle introduction system constructed and arranged to receive a fluid material containing a plurality of target structures and non-target structures in order to add custom-shaped particles thereto; an agitation system arranged in fluid connection with the particle introduction system to receive a fluid material containing a plurality of the target structures, the non-target structures, and the custom-shaped particles and, the agitation system being structured to agitate the structures and particles in the fluid material; an aggregate isolation system arranged in fluid connection with the agitation system to receive a fluid material from the agitation system through which the aggregates are concentrated and separated; and a disaggregation system arranged in fluid connection with the aggregate isolation system to receive a fluid material from the aggregate isolation system and through which aggregates are disaggregated. The at least a portion of the surface of each of the custom-shaped particles has a shape-complementary surface with at least a portion of a surface of a target structure.

BRIEF DESCRIPTION OF THE DRAWINGS

The invention is better understood by reading the following detailed description with reference to the accompanying figures in which.

DETAILED DESCRIPTION

Figure 1A:
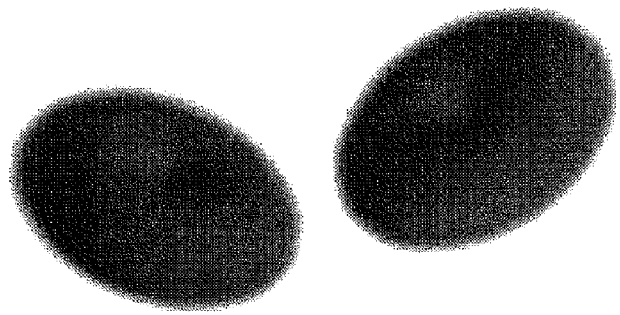
FIG. 1(a) is a schematic illustration of two human red blood cells (orthographic view of a 3-dimensional computer rendering) which have a shape and size that represent a target structure and from which a custom-shaped particle can be designed according to an embodiment of the current invention.

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose.

According to an embodiment of the current invention, by designing and making dispersions of custom-shaped colloidal particles that have complementary dimensions, shapes, and interactions to the surfaces of specific target structures (e.g. biostructures) in a complex mixture, custom-shaped particles naturally bind or are induced to bind to a particular target structure or to a plurality of target structures, without the same particles binding to non-target structures also present in the mixture. Such complementary-shaped particles typically possess a material property that also provides a convenient means of separation after custom-shaped particles selectively bind to one or more target structures. For instance, in some embodiments of the current invention, custom-shaped particles contain a fluorescent dye for identification and/or magnetically-responsive nanoparticles that enable and facilitate magnetic separations. This combination of a designed shape and customized material properties of the particles can provide a means for efficiently tagging, identifying, isolating, separating, and sorting specific target structures (e.g. cell types) from the rest of a complex mixture or dispersion according to some embodiments of the current invention. Typically, a separation can be performed without disrupting any biological function of the target structures, thereby keeping them viable for further study and identification. In some embodiments of the current invention, the binding of custom-shaped particles to target structures can be reversible, so that it is possible to subsequently separate target structures from the custom shaped particles and to re-use the custom-shaped particle if desired. For example, target structures can range from microscale cells to nanoscale organelles and sub-cellular structures as well as non-biological target structures.

According to an embodiment of the current invention, specific target structures can be separated and sorted from other non-target structures in a complex mixture, where this complex mixture is comprised of target structures and non-target structures. These target structures and non-target structures can be objects having maximum dimensions in the range from a few nanometers to hundreds of micrometers; these objects can be dispersed as a complex mixture in a continuous liquid phase. Herein, this size range is sometimes referred to as colloidal, recognizing that the size range of interest actually extends up to sub-millimeter length scales (i.e. beyond the typical upper limit of a few microns in the conventional definition of colloidal). The target structures and non-target structures can be dispersed and/or suspended in a viscous liquid, biological liquid, buffer solution, viscoelastic material, or a soft material. Some embodiments of the current invention provide a process for identifying and/or separating target colloidal structures from non-target colloidal structures based on differences in attractive interactions of each of the structures with custom-designed shape-complementary colloidal particles that have at least a surface which is chosen to and/or designed to conform to (i.e. mate with) the size and shape of at least one particular target structure or target subset of structures in the mixture. Cells represent an important class of biological structures, also referred to herein as biostructures, and a complex mixture of biostructures can include mixtures containing different types of cells that may have different physical dimensions and shapes.

According to an embodiment of the current invention, it can be desirable to identify the dimensions and shapes of the outer surface contours of the target colloidal structures. This may require a form of microscopy (electron microscopy, scanning probe microscopy, and/or optical microscopy) to observe the dimensions, shapes, and contours of at least the target structures in the mixture according to this embodiment of the current invention. For example, certain cell types, such as normal human red blood cells, have uniform sizes and regular shapes. Once a target structure is identified and characterized in terms of shape and size by a three-dimensional surface (or at least a portion thereof), it is also desirable to also identify and characterize the three-dimensional surfaces describing non-target structures that may also be present in the mixture. Whenever possible, a differentiating shape and size contour (i.e. geometrical surface feature) is identified between target and non-target structures, so that design of the shape of the complementary colloidal particle can be made based on this differentiating shape and size feature of the surfaces of the structures.

According to an embodiment of the current invention, given prior knowledge of the three-dimensional contours of the desired target structure or structures (or of portions of such contours) to be separated, one or more types of colloidal particles having customized shapes and sizes are designed, produced, and/or selected. These custom-shaped colloidal particles have at least one surface that is complementary to a portion of the surface contours of the target structure or structures. In addition, the designed shape of the custom-shaped particle does not also have a complementary surface that matches the size and shapes of non-target structures in the mixture according to this embodiment, which are not among the target structures which are desired to be separated. A particle shape that is properly designed according to some embodiments of the current invention would be most effective at achieving shape-specific binding, identification, separation, and sorting if it has at least a portion of its surface that is complementary to the size and shape of the target structure to be separated without also having any portion of its surface to be complementary in size and shape to non-target structures that are to remain in the mixture and are not to be separated. A shape-complementary particle can facilitate a large proximate surface area or contact surface area between the shape-complementary particle and the target structure when the shape-complementary particle and target structure are configured in at least one relative position and one relative orientation. For purposes of clarifying terminology used in the specification, a custom-shaped particle bound to a target structure is referred to as an aggregate or equivalently as an assembly.

According to some embodiments of the current invention, the selecting, designing, producing, and/or adding custom-shaped particles into a complex mixture to provide at least a portion of a custom-shaped particle's surface that is shape-complementary and size-complementary with at least a portion of the surface of a desired target structure and that facilitates binding of a custom-shaped particle with at least a portion of the surface of a desired target structure represents a significant advance over prior art. By contrast, a primitive method of colloidal separation (Mason, T. G. Osmotically driven shape dependent colloidal separations. Phys. Rev. E 2002, 66, 060402/1-4) does not involve selecting, designing, producing, or introducing custom-shaped particles into a mixture based on pre-existing spatial information about a desired target structure. Moreover, this primitive method does not provide a custom-shaped particle that enables preferential aggregation of target structures with custom-shaped particles that facilitate separation of said target structure-complementary particle aggregate from the rest of the complex mixture.

In some embodiments of the current invention, certain cell types may be target structures (i.e. target biostructures), and certain other cell types may be non-target structures (i.e. non-target biostructures).

According to an embodiment of the current invention, after designing a custom-shaped particle to have at least a portion of its surface that is shape complementary and size complementary to the desired target structure, a dispersion of the custom-shaped colloidal particles is produced. This dispersion can contain a plurality of particles having the desired shape and size—at least as many custom-shaped particles having complementary surface geometries as there are target structures, but more desirably an excess of custom-shaped particles compared to the number of target structures in the complex mixture. This process of mass production of custom-shaped particles can be accomplished by a diversity of methods that currently exist, as described and referenced in the aforementioned discussion of related art. A top-down synthesis (e.g. fabricating particles lithographically), bottom-up synthesis (e.g. making spheres, ellipsoids, cubes, or nanotubes through reactions of molecular precursors), and a combination thereof can be used to fabricate custom-shaped particles that are shape-complementary and size-complementary.

According to some embodiments of the current invention, the material composition of the custom-shaped particles contains fluorescent dyes and nanoparticles, including quantum dots for imaging detection and magnetically responsive nanoparticles (e.g. iron oxide) to enable and facilitate magnetic separations. In some embodiments of the current invention, the custom-shaped particles also have a significant density difference with the continuous suspending fluid, thereby enabling and facilitating gravitational or centrifugal separations. In addition, in other embodiments of the current invention, the custom-shaped particles have a difference in refractive index (i.e. polarizability) compared to that of the surrounding liquid, enabling separations made by applying electric fields (e.g. dielectrophoresis) and optical fields (e.g. laser tweezers). In another embodiment of the current invention, the custom-shaped particles have a surface charge (or a plurality of patches of surface charge) that enable them to be separated by electrophoresis. Typically, the surfaces of the custom-shaped particles can be decorated with surfactants, polymer, biopolymers, proteins, polypeptides, co-polypeptides, nanoparticles, and other types of species to also potentially promote or enhance binding of the particles to the particular target structures that have been selected for separation. In particular, the surfaces of custom-shaped particles can be decorated in a manner to control surface roughness, thereby permitting the use of roughness-controlled depletion attractions to facilitate more control over the aggregation between the custom-shaped particles and desired target structures.

According to another embodiment of the current invention, a stable dispersion of custom-shaped and sized particles is mixed with the complex dispersion of a variety of cell types, such as is present in human blood. Concurrent with and subsequent to the mixing, custom-shaped particles, target structures, and non-target structure translate and rotate in the fluid as they are driven by diffusion, flow, convection, and/or agitation. As custom-shaped particles encounter target structures, non-target structures, and other custom-shaped particles through this motion, a portion of the custom shaped particles selectively bind to the surfaces of the desired target structure (e.g. cell type or subclass of cell types). In some embodiments of the current invention, it is desirable to design the surface coatings of the custom-shaped particles to create attractive interactions with certain portions of the surfaces of target structures.

In an embodiment of the current invention, an attractive interaction that is used to bind custom-shaped particles to target structures is the depletion attraction, which depends on the shapes and sizes of the custom-shaped particles. The strength of the depletion attraction between two surfaces is related to geometry and entropy. Typically, colloidal structures known as depletion agents, which are typically neither target structures nor shape-designed particles, are either present in the fluid material (i.e. complex mixture) or are added to induce the attraction. For instance, a depletion attraction that is strong enough to overcome thermal excitations of a particle and a target structure, causing strong binding between the particle and target structure, can arise from non-target structures that may already be present in the complex mixture. Alternatively, a depletion agent can be introduced into the complex mixture containing custom-shaped particles and target structures at a concentration that is sufficient to create desired depletion attractions. In another embodiment of the current invention, particle coatings and materials can be designed to facilitate binding between the custom-shaped particles and the desired target structures. After mixing custom-shaped particles that are shape-complementary and size-complementary with the complex mixture containing target structures and non-target structures, a combination of diffusion and convection can cause the particles to encounter them and effectively find a configuration that provides for mating of a portion of the surface of the complementary-shaped and complementary-sized particles with the target structures. The sampling of configurations is not instantaneous and aggregation of the custom-shaped particles with the target structures occurs over a duration of time that is at least long enough that the custom-shaped particles encounter the target structures at least once, and preferably much more than once. The time over which substantial aggregation occurs depends upon the concentration of the desired target structures, the concentration of the custom-shaped particles, the strength of the attractive interaction, the accessibility of a mating configuration, and the probability of orientations of a custom-shaped particle relative to the desired cell that will permit the complementary surfaces to approach and create a strong enough attractive interaction for binding to occur effectively.

In an embodiment of the current invention, complementary-shaped and complementary-sized particles are added to the complex mixture containing target structures and then a depletion agent is subsequently added to cause a depletion attraction. Suitable depletion agents include polymers (e.g. polyethylene glycol—PEG), micelles, nanoparticles, nanoemulsions, or a combination thereof according to some embodiments of the current invention. One or more depletion agents having a pre-specified maximum spatial dimension are added in sufficient quantity to the complex mixture of custom-shaped particles and target structures to create a depletion attraction between the custom-shaped particles and the target structures that depends on the surface geometry and will cause the desired target structures to be attracted to and effectively bound to custom-shaped particles. Waiting a sufficient time after mixing the custom-shaped particles with the target structures can be desirable in some embodiments so that the custom-shaped particles and target structures are able to encounter each other frequently enough for a specific target structure to bind with a custom-shaped particle with a strong enough binding energy to inhibit unbinding due to thermal agitation and/or externally imposed agitation.

In some embodiments of the current invention, the energy associated with a single particle-cell attraction, or binding energy, is significantly stronger than thermal energy, $k_B T$, where T is the temperature and $k_B$ is Boltzmann's constant, so that the particle and cell remain attracted and bound to each other despite continuously occurring thermal excitations. The strength of the depletion attraction can be influenced by the degree of complementarity of at least a portion of a custom-shaped particle's surface with at least a portion of a target structure's surface, and the strength of the attraction can also be varied by controlling the concentration and size of a smaller colloid added as a depletion agent. In addition, a pre-specified surface roughness can be designed into the surfaces of custom-shaped particles to control depletion-induced attractions between portions of the surfaces of the custom-shaped particles and portions of the surfaces of target structures.

In some embodiments of the current invention, more than one target structure can become bound to a single custom-shaped particle. A custom-shaped particle can have one or more shape-complementary and size-complementary portions of its surface that provide a capacity for the custom-shaped particle to bind with one or more target structures.

In an embodiment of the current invention, after custom-shaped particles and target structures have bound together, it is desirable to separate out aggregates of custom-shaped particles that have bound to target structures using a variety of separation methods. By designing the composition of the custom-shaped particle to have a significant density difference with respect to the continuous liquid phase (i.e. suspending liquid) compared to the density difference of the other types of target structures with respect to the continuous liquid phase, the aggregates can be separated and any unbound custom-shaped particles by relying upon centrifugation, gravitational creaming, or sedimentation. Alternatively, in another embodiment of the current invention, by producing custom-shaped particles that contain iron-oxide nanoparticles or other magnetically sensitive materials, the separation of aggregates and any unbound custom-shaped particles is accomplished by applying a magnetic field and/or magnetic field gradient, which causes the aggregates and any unbound custom-shaped particles to move to a particular region of the container, thereby concentrating them. In yet another embodiment, the difference in hydrodynamic drag forces between unbound target structures and aggregates containing target structures facilitates sorting target structures from non-target structures in a microfluidic device.

In another embodiment of the current invention, once separated, target structures that are bound to custom-shaped particles can be unbound from the custom-shaped particles, and the custom-shaped particles can be separated from the target structures and re-used for subsequent separations. In the case of depletion attractions, this can be accomplished by the simple reduction in concentration of the depletion agents through a process of dilution with the pure continuous phase or an appropriate buffer solution that would maintain biological viability of biological target structures. A reduction in the concentration of a depletion agent is typically sufficient to cause the unbinding of the custom-shaped particles with the desired target structures. Custom-shaped particles that exhibit a density difference with respect to the continuous phase which is significantly different than the target structure's density difference with respect to the continuous phase are suitable for separation by centrifugation and/or gravitational forces, thereby causing more rapid sedimentation or creaming of the particles relative to the target structures. Custom-shaped particles containing magnetically responsive components and that can move more rapidly than the target structures in response to magnetic field gradients can be separated out from the target structures by applying a magnetic field or a magnetic field gradient. In some embodiments of the current invention, custom-shaped particles that are recovered in this manner are cleaned by dialysis and solvent exchange and then re-used in subsequent separation processes. A separation process involving custom-shaped particles can be performed in a manner that enables separated biological target structures, such as cells of a certain specific cell type, to remain viable throughout and after the separation process.

Figure 1B:
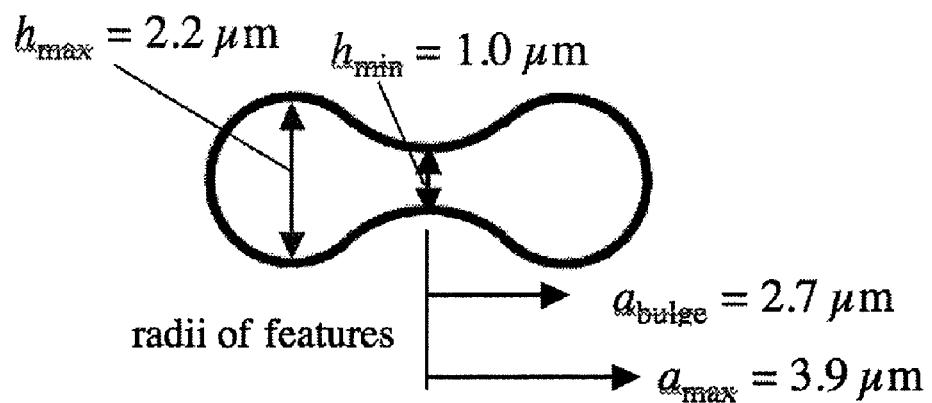
FIG. 1(b) is a schematic illustration of a human red blood cell (cross-sectional view through a mid-section), which is a target structure according to an embodiment of the current invention. Average dimensions for thickness and radii are provided, from which a custom-shaped particle can be designed according to an embodiment of the current invention.

Example Embodiment of Separating Normal Human Red Blood Cells from Whole Human Blood According to an embodiment of the current invention, normal adult human red blood cells are separated from other miroscale and nanoscale biostructures that are typically present in normal adult human blood. Normal human red blood cells, shown schematically in FIG. 1(a), which are a component of the blood of normal human adults, have the following average dimensions: primary radius from the center of the red blood cell to the outer edge (i.e. effective disk outer radius) $<a>=3.9$ μm, minimum central thickness of $h_{min}=1.0$ μm between the two central dimples, and maximal thickness $h_{max}=2.2$ μm which occurs at an average radius $<a_{bulge}>=2.7$ μm, as shown in FIG. 1(b).

Figure 2A:
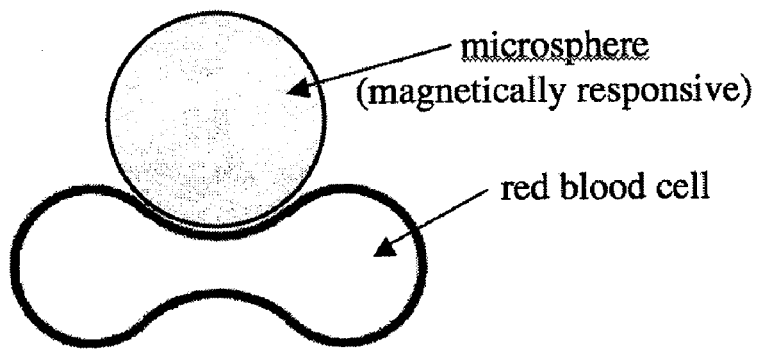
FIG. 2(a) is a schematic illustration (cross-sectional view through a mid-section) of a spherical shape-complementary and size-complementary particle (top) corresponding to a human red blood cell (bottom) that has been selected according to an embodiment of the current invention. The composition of the spherical particle is magnetically responsive in order to facilitate subsequent separations.
Figure 2B:
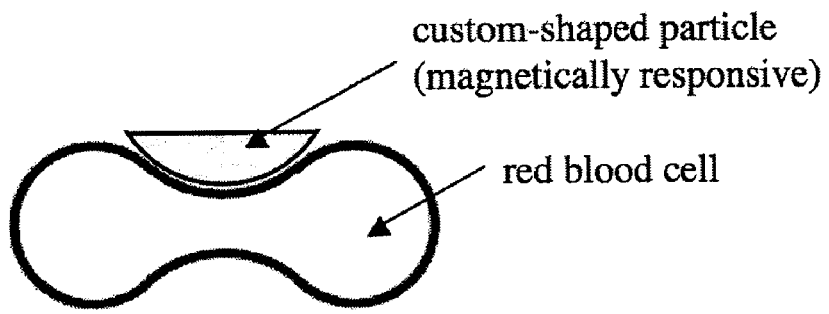
FIG. 2(b) is a schematic illustration (cross-sectional view) of a custom-shaped particle (top) that has been designed to have shape-complementary and size-complementary portion of its surface corresponding to a human red blood cell (bottom) according to an embodiment of the current invention. The composition of the custom-shaped particle is magnetically responsive in order to facilitate subsequent separation.
Figure 2C:
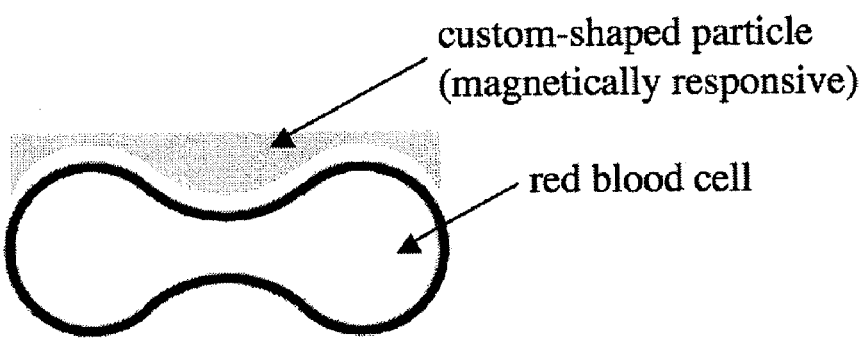
FIG. 2(c) is a schematic illustration (cross-sectional view) of a custom-shaped particle (top) that has been designed to have shape-complementary and size-complementary portion of its surface corresponding to a human red blood cell (bottom) according to an embodiment of the current invention. The composition of the custom-shaped particle is magnetically responsive in order to facilitate subsequent separation.

According to some embodiments of the current invention, particles are selected, designed, and/or fabricated in order to provide a complementary size and/or surface contour characteristics that would facilitate size and/or shape-specific binding to a human adult red blood cell, as shown in FIGS. 2(a), 2(b), and 2(c). Custom-shaped particles having a slab-like shape or a half-lozenge like-shape are viable design structures that are capable of facilitating binding with normal red blood cells at a site corresponding to the concave dimples in their surfaces.

Figure 3:
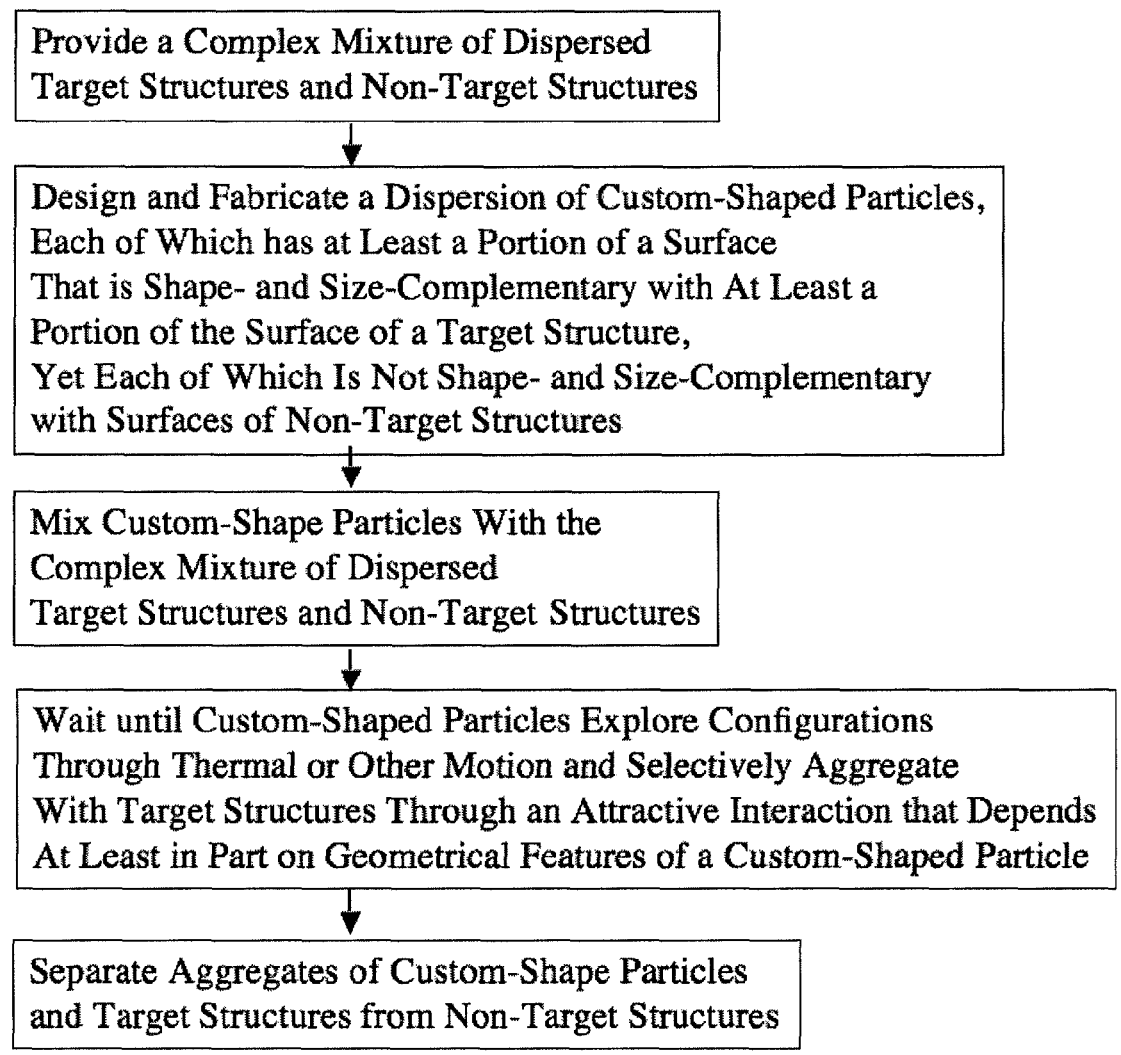
FIG. 3 is a schematic illustration of a process for designing and using custom-shaped particles to separate target structures from non-target structures according to an embodiment of the current invention.

According to an embodiment of the current invention, a procedure for separating normal red blood cells (a particular target structure for this embodiment) from whole blood (a dispersion of target structures and non-target structures) is shown schematically in FIG. 3. A dispersion of shape-complementary particles that are magnetically responsive is mixed with a liquid containing the blood cells (e.g. whole human blood or a derivative solution of whole human blood). If a high efficiency of separation is desired, it is typically useful to add an excess number of custom-shaped particles compared to the number of target structures (i.e. red blood cells) that are in the complex mixture. If custom-shaped particles do not bind to the normal blood cells without the addition of a binding agent to the mixture, then it may be necessary to introduce an agent to cause a strong enough attraction between the custom-shaped particles and the red blood cells for the binding to occur. An example of such a binding agent that can cause the desired attractions is a depletion agent (e.g. including but not limited to polymers, micelles, nanoparticles, and nanodroplets).

Figure 4A:
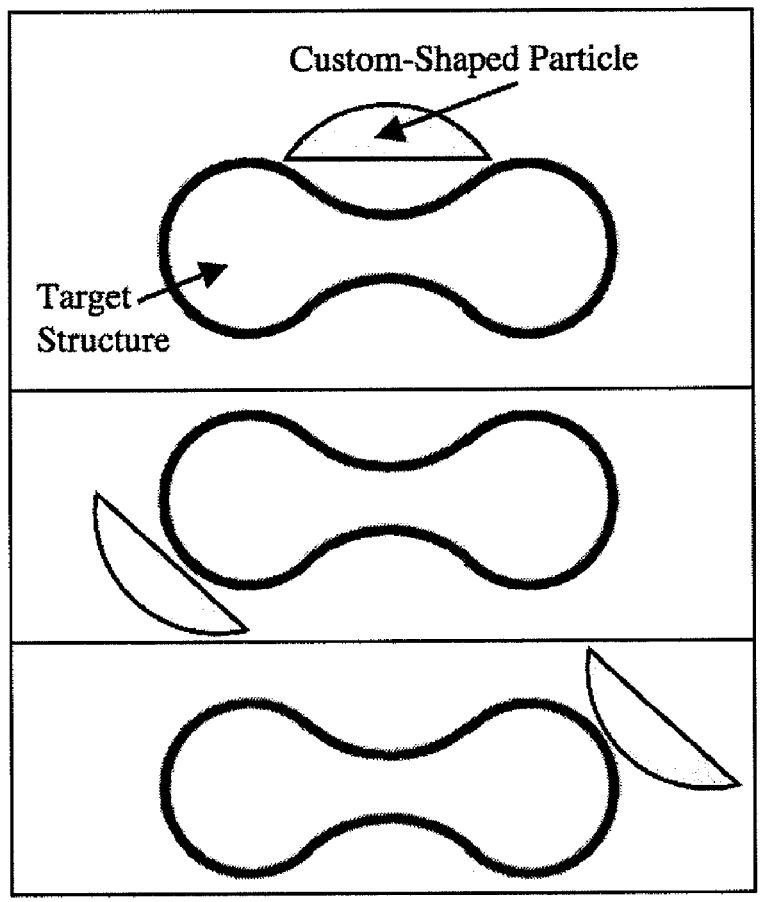
FIG. 4(a) is a schematic illustration (cross-sectional view) of three possible local configurations (top, middle, and bottom frames) of a custom-shaped particle (i.e. a truncated arc shown as filled) relative to a target structure (i.e. a red blood cell shown in outline) which could occur as custom-shaped particles and target structures move during and after mixing custom-shaped particles with a complex mixture containing a dispersion of target structures, according to an embodiment of the current invention. In all three cases shown, the relative configurations do not provide a surface area of interaction that is large enough to facilitate binding of the custom-shaped particle to the target structure, since the shape- and size-complementary portion of the custom-particle's surface is not positioned and oriented in a manner that mates with at least a portion of the target structure.
Figure 4B:
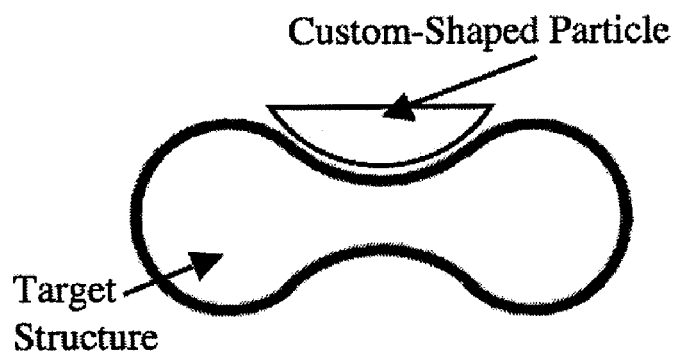
FIG. 4(b) is a schematic illustration (cross-sectional view) of a local configuration of a custom-shaped particle (i.e. a truncated arc shown as filled) relative to a target structure (i.e. a red blood cell shown in outline) which could occur as custom-shaped particles and target structures move during and after mixing custom-shaped particles with a complex mixture containing a dispersion of target structures, according to an embodiment of the current invention. As shown, the relative configuration provides a surface area of interaction that is sufficiently large that it facilitates binding of the custom-shaped particle to the target structure, since the shape- and size-complementary portion of the custom-particle's surface is positioned and oriented in a manner that mates with at least a portion of the target structure.
Figure 5A:
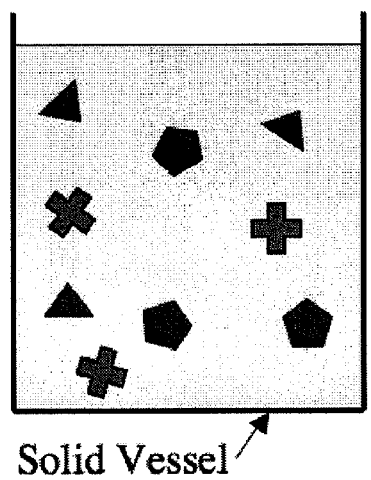
FIG. 5(a) is a schematic illustration of a complex mixture containing a plurality of a chosen target structure (green crosses), each of which has a similar shape and size, and a plurality of non-target structures, each of which belong to two types of non-target shapes (red triangles and purple pentagons), wherein both target structures and non-target structures are dispersed in a first fluid material (blue background), according to an embodiment of the current invention. Separation of the target structures from the non-target structures is desired.
Figure 5B:
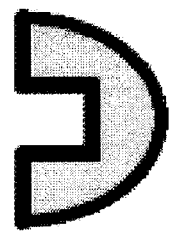
FIG. 5(b) is a schematic illustration of a target structure that is to be separated and sorted from non-target structures in a complex mixture, according to an embodiment of the current invention.
Figure 5C:
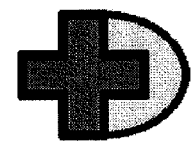
FIG. 5(c) is a schematic illustration of a shape-complementary particle (yellow C-shape having a square interior region) bound to a target structure (green cross) in a mating shape-complementary and size-complementary manner, according to an embodiment of the current invention. Typically, a geometrical feature of the surface of a custom-shaped particle is designed to provide a larger surface area of interaction with a target structure in a possible configuration, compared to surface areas of interaction with non-target structures in a variety of configurations. Typically, other geometrical features of the surface of the custom-shaped particle are designed to avoid produce a large surface area of interaction with non-target structures. A binding energy associated with the attractive interaction between the custom-shaped particle and the target structure, which can depend on the area of proximate surfaces between them, is typically large enough so that the aggregate formed is typically not disaggregated by thermal agitation or applied agitation that enables the custom-shaped particles to move and rotate into proximity with target structures and non-target structures. Furthermore, typically, the custom-shaped particle possesses a shape and surface properties, such as surface charge, that inhibits the formation of aggregates of custom-shaped particles with other custom-shaped particles.
Figure 5D:
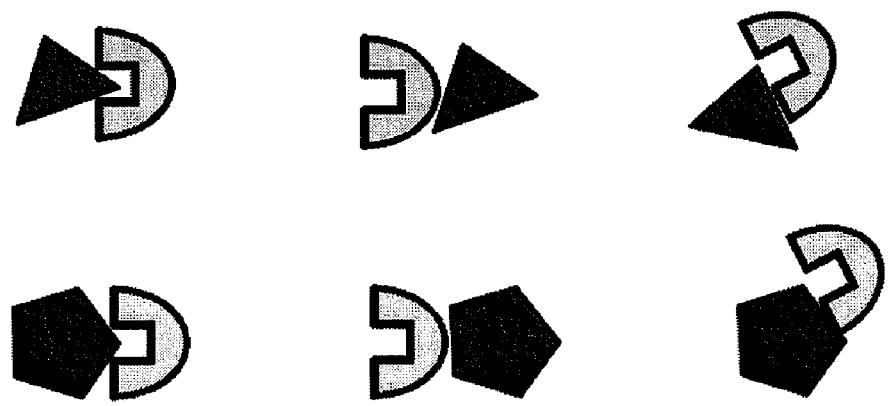
FIG. 5(d) is a schematic illustration of six different cases of relative configurations of a custom-shaped particle with respect to non-target structures, according to an embodiment of the current invention. It is typically desirable to design surface geometrical features of a custom-shaped particle to provide a smaller area of near proximity of surface regions between custom-shaped particles and non-target structures when they undergo encounters in a variety of relative positions and orientations. Typically, the interaction between a custom-shaped particle and a non-target structure is not sufficiently strong so that an aggregate of a custom-shaped particle with a non-target structure is not formed while in the presence of thermal agitation or applied agitation.
Figure 5E:
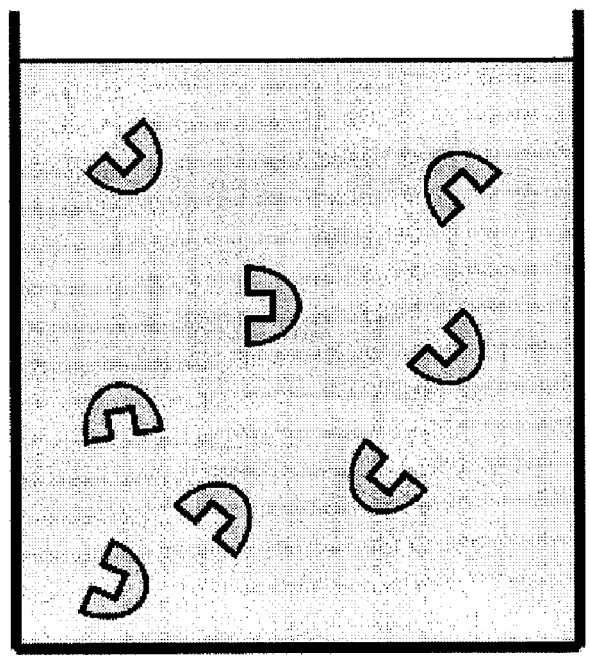
FIG. 5(e) is a schematic illustration of a dispersion of custom-shaped particles that have been designed to have shape-complementary and size-complementary features with a target structure, according to an embodiment of the current invention. Typically, the fluid base of the dispersion of custom-shaped particles is miscible with the fluid base of the complex mixture containing target structures and non-target structures. It is typically desirable for custom-shaped particles to possess a material property that enables them to be easily isolated, concentrated, and separated, and the custom-shaped particle possesses a property of being responsive to an externally applied magnetic field.
Figure 5F:
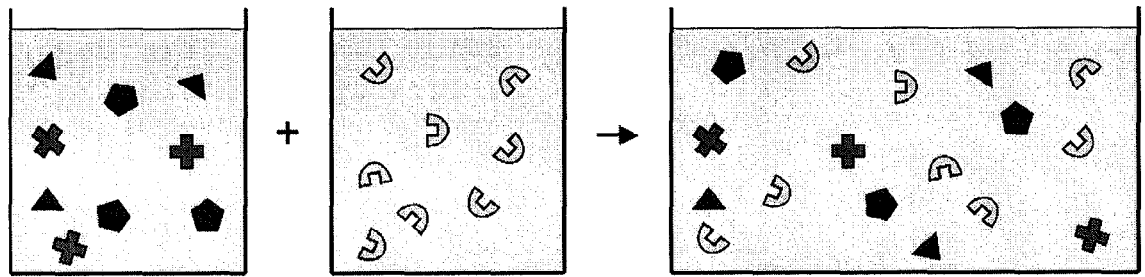
FIG. 5(f) is a schematic illustration of combining a dispersion of custom-shaped particles to a complex mixture containing target structures and non-target structures, according to an embodiment of the current invention.
Figure 5G:
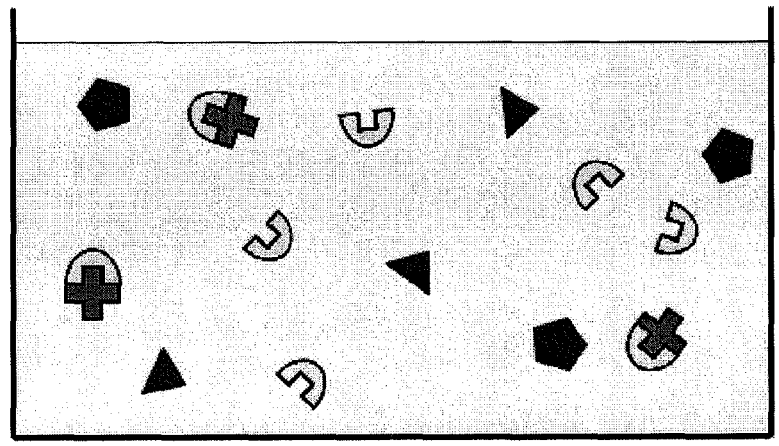
FIG. 5(g) is a schematic illustration of binding of custom-shaped particles to target structures but not to non-target structures as a result of differences in attractive interactions and after particles and structures have sampled a variety of positional and orientational configurations that lead to particle-structure encounters, according to an embodiment of the current invention. Typically, shape-complementary and size-complementary features of the custom-shaped particles facilitate binding with the target structures to form aggregates but not with the non-target structures. For instance, the binding attraction can be a depletion attraction induced by the addition of a depletion agent.
Figure 5H:
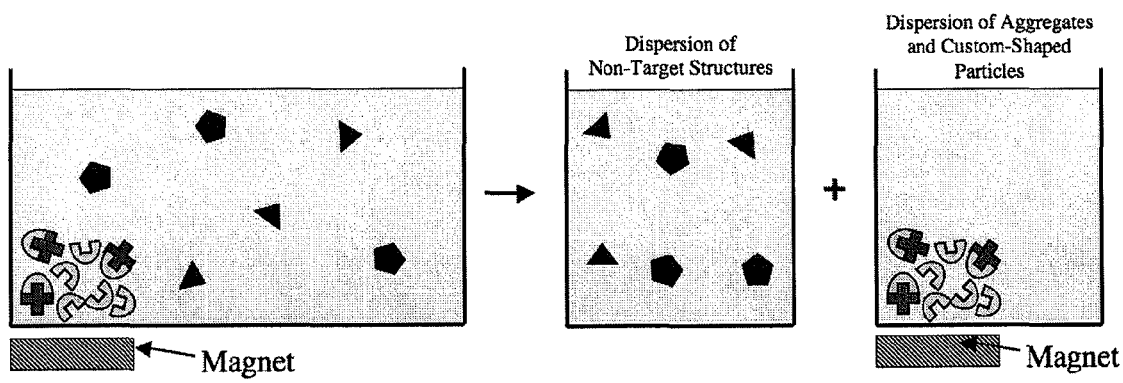
FIG. 5(h) is a schematic illustration of isolation and separation of a plurality of aggregates, each of which contains at least a custom-shaped particle and a target structure, and any remaining unbound custom-shaped particles, in a complex mixture according to an embodiment of the current invention. Typically, the isolation and separation is accomplished by applying an external field, such as a magnetic field produced by a magnet, as shown, to spatially segregate the aggregates of custom-shaped particles with target structures and any unbound custom-shaped particles from the non-target structures. For example, it is possible to separate the dispersion containing non-target structures by pouring into a second vessel while aggregates are held and retained in a first vessel by a magnetic field that is produced by a magnet.
Figure 5I:
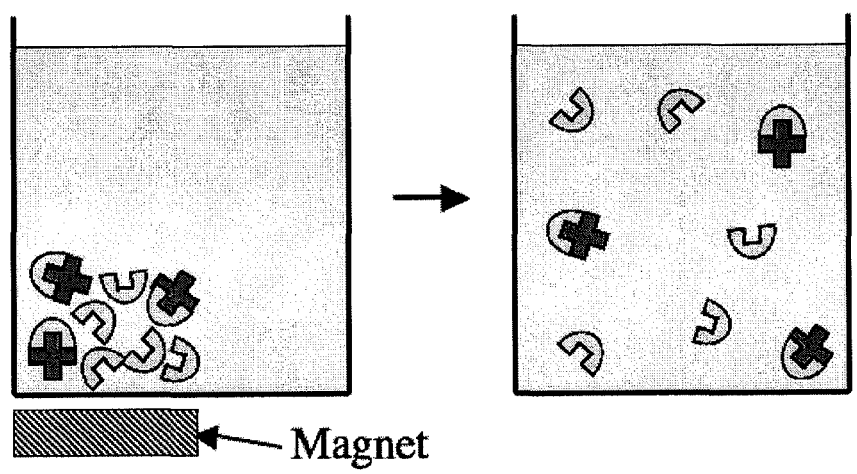
FIG. 5(i) is a schematic illustration of re-dispersing aggregates of custom-shaped particles and target structures and any unbound custom-shaped particles by removing a previously applied external field that had been used to accomplish a separation, according to an embodiment of the current invention.
Figure 5J:
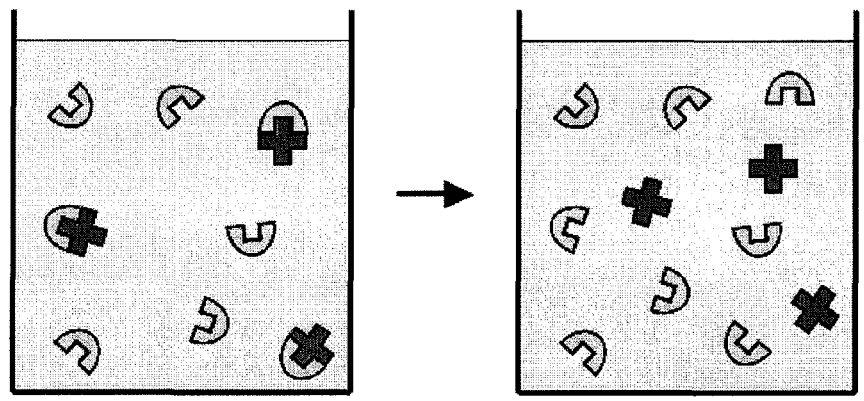
FIG. 5(j) is a schematic illustration of disaggregation (i.e. unbinding) of custom-shaped particles and target structures caused by reducing or removing the attractive interaction between them, according to an embodiment of the current invention. For example, in the case of a depletion attraction, the concentration of a depletion agent can be reduced by at least one of a dilution, a filtration, or a dialysis, and this can reduce the binding energy such that thermal agitation is sufficient to cause the target structures to unbind from the custom-shaped particles.
Figure 5K:
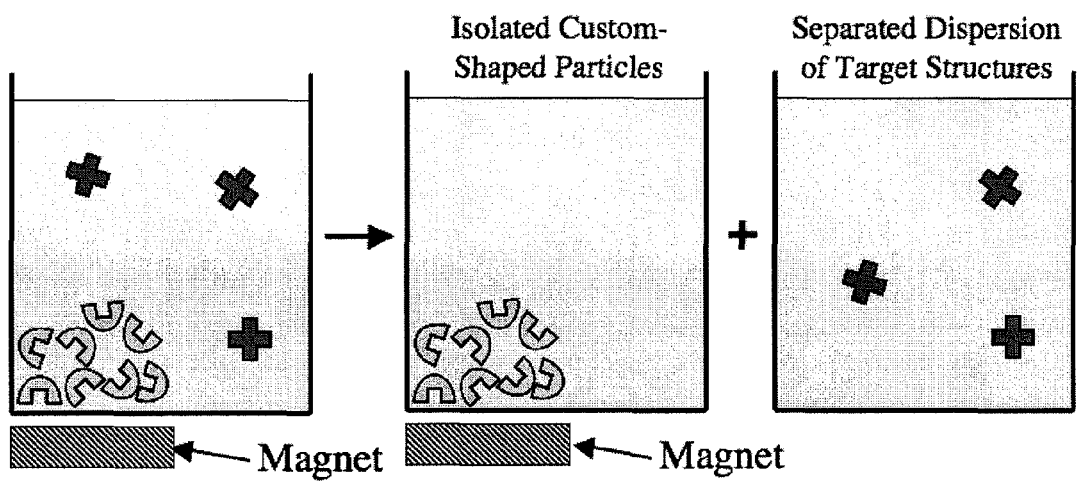
FIG. 5(k) is a schematic illustration of isolating and separating the unbound custom-shaped particles from the target structures, to yield a dispersion of nearly pure custom-shaped particles and a dispersion of nearly pure target structures, according to an embodiment of the current invention. As shown, a magnetic field produced by a magnetic is used to concentrate and hold magnetically responsive custom-shaped particles while a dispersion of target structures is transferred to a separate vessel.
Figure 5L:
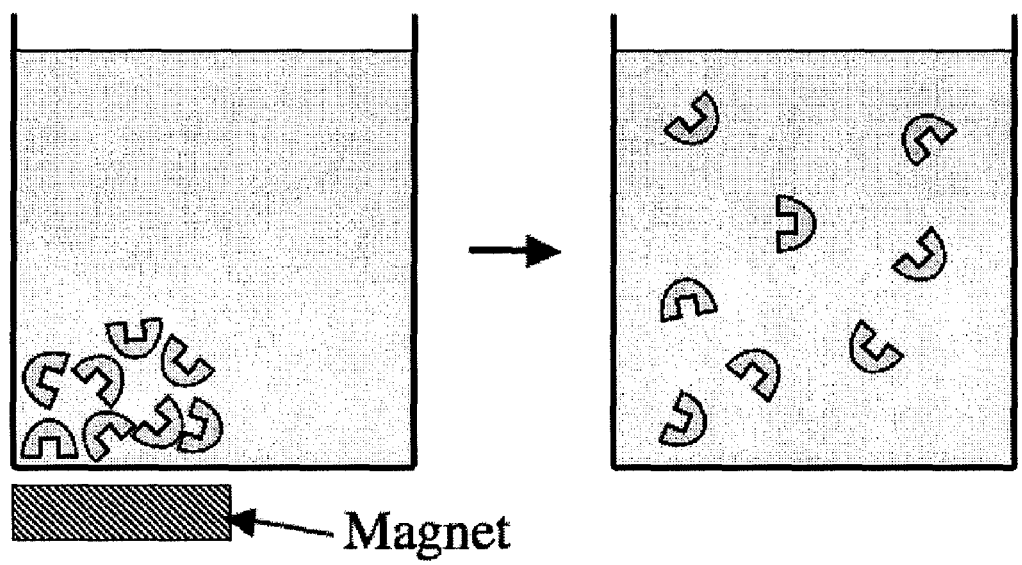
FIG. 5(l) is a schematic illustration of recovering and re-dispersing custom-shaped particles subsequent to the step shown in FIG. 5(k), according to an embodiment of the current invention. Typically, recovered custom-shaped particles can be re-used for subsequent separations of target structures from non-target structures. As shown in this example, this is accomplished by removing the magnet (i.e. by removing the magnetic field) that has been previously used to isolate and concentrate magnetically responsive custom-shaped particles.

According to an embodiment of the current invention, local non-binding relative configurations of the custom-shaped particle with respect to target structures are sampled due to motion caused by thermal excitations, fluid flows, convection, turbulence, or other sources of agitation. Three examples of local non-binding configurations are shown in FIG. 4(a). As different relative configurations of the custom-shaped particles, target structures, and non-target structures are sampled over time, a shape- and size-complementary portion of a custom-shaped particle moves into close relative proximity with a mating portion of a target structure in a manner that causes an attraction that is typically large enough to cause binding and inhibit their subsequent separation. An example of a local binding configuration of a custom-shaped particle with a red blood cell is shown in FIG. 4(b). Typically, it is desirable to allow sufficient time for the cells to form aggregates with the custom-shaped particles. In some embodiments of the current invention it is desirable for the type of binding and aggregation to be reversible, so that the custom-shaped particles and target structures can be unbound and disaggregated at a later time without damage to the target structures.

In some embodiments of the current invention, an energy associated with the attraction is proportional to an area corresponding to a surface of one dispersed object that is in close proximity with a surface of a second dispersed object. Typically, this is true for depletion attractions. Consequently, relative configurations that are non-mating provide only a small proximate area of contact between the dispersed objects. Typically, in the absence of external agitation, if the energy associated with the attraction is less than or near thermal energy, $k_B T$, no aggregation of the dispersed structures can occur because thermal fluctuations can effectively inhibit binding. By contrast, typically, a relative configuration that is mating (i.e. shape-complementary and size-complementary) provides a larger proximate area between the surfaces of a custom-shaped particle and the target structure. Consequently, an attractive binding energy that is significantly more than thermal energy, $k_B T$, is created, so the custom-shaped particle does form an aggregate with a target structure because the attractive binding interaction overcomes thermal fluctuations.

According to an embodiment of the current invention, a reversible type of binding and aggregation is created by a depletion attraction.

According to another embodiment of the current invention, a flow, an agitation, a convective mixing, an osmotic pressure, an applied external field, or a combination thereof is used to raise the frequency of encounters between custom-shaped particles and target structures in a variety of relative positions and orientations beyond what is induced by Brownian motion (i.e. thermal diffusion).

In another embodiment of the current invention, the cell-particle aggregates are separated and concentrated from the rest of the complex mixture containing the blood cells using external forces (e.g. created by an applied external magnetic field). Such cell-particle aggregates are then placed in a separate container or otherwise physically segregated from the rest of the complex mixture.

According to a further embodiment of the current invention, once separated from the original liquid, the concentration of the depletion agent is reduced so that disaggregation (i.e. unbinding) of the cell-particle aggregates occurs. This reduction in concentration can be achieved, for example, by dialysis or by simple dilution of the dispersion of cell-particle aggregates. Application of an external field (e.g. a magnetic field), or a gradient thereof, is used to separate and concentrate the shape-complementary particles from the cells, and these particles are removed from the dispersion of cells that have the desired size and shape. The shape-complementary particles are further processed (e.g. washed) and re-used in subsequent separations. Moreover, cell viability can be maintained throughout the entire separation process, yielding live cells that function normally.

According to an embodiment of the current invention, a cell separation process is carried out in a bulk container. According to another embodiment, a cell separation process is carried out in a microfluidic device. External fields useful for separation include electric, magnetic, and gravitational fields, as well as effective gravitational fields produced by centrifugation.

According to an embodiment of the current invention, a cell separation process is used to separate normal blood cells from diseased blood cells that can occur due to blood diseases that cause conformational changes in the shapes of the blood cells (e.g. sickle-cell anemia).

According to another embodiment of the current invention, particles that have shapes designed to bind to diseased sickle-cells, rather than normal red blood cells, are used to separate out the diseased cells from the whole blood or a derivative of whole blood.

In another embodiment of the current invention, custom-shaped particles are used to purify contaminated blood by separating out viable and beneficial blood cells from other unwanted components in donated blood, such as viruses, spirochetes, tumor cells, and disease-causing components, thereby providing a cleaner blood supply for transfusions.

In another embodiment of the current invention, custom-shaped particles are used to separate a specific type of bacterial cells from a mixture of different types of bacterial cells based on differences of average shape and size characteristics of the different cell types In another embodiment of the current invention, custom-shaped particles are used to separate and isolate specific target cell types from mixtures of plant cells, animal cells, bacterial cells, and fungal cells.

Example Embodiment of Separating Specific Organelles from Lysed Cells

In an embodiment of the current invention, custom-shaped particles are used to separate and sort the components of a lysate, which is a solution containing the contents of lysed cells. Typically, a lysate is mixed with a dispersion of custom-shaped particles. Typically, by designing custom-shaped particles that are complementary in shape and size to the surfaces of desired organelles, geometry-dependent attractions, such as the depletion attraction, can be used to create a desired binding between custom-shaped particles and certain target organelles in a lysate. Typically, the geometry-dependent attractions are stronger between the desired organelle and the custom-shaped particles (i.e. in certain accessible particle-organelle configurations), compared to that between other organelles and custom-shaped particles, thereby providing a means for creating particle-organelle aggregates that can be effectively removed from the mixture of the particle dispersion with the lysate.

In some embodiments of the current invention, since sub-micron organelles in a lysate are typically smaller than cells, it is typical to use a high-precision form of lithography that offers a smaller minimum feature size in order to create custom-shaped particles that are suitable for separating organelles, at least compared to larger cells. Typically, sub-micron custom-shaped particles can be created through a variety of top-down nanofabrication methods, including but not limited to: optical lithography, electron-beam lithography, dip-pen lithography, nanocontact printing, relief deposition templating, and nanoimprinting. In another embodiment of the current invention, bottom-up synthetic methods for fabricating custom-shaped particles could also be used, although control over the shapes of the resulting particles is typically not as versatile or well controlled as with top-down lithographic methods.

In an embodiment of the current invention, a specific class of organelles (e.g. mitochondria) can have a variety of shapes and sizes (see e.g. Voeltz, G. K. and Prinz, W. A. Sheets, ribbons, and tubules—how organelles get their shape. Nature Reviews, 2007, 8, 258-264). Moreover, their outer membranes can be flexible, potentially enabling them to deform to some degree. Thus, there is typically a polydispersity both in shape and size of even the potential target organelle. This polydispersity typically reflects the maturity of the organelle. Therefore, by using custom-shaped particles, it is typically possible to selectively separate a subset of a particular type of organelle. This separation may be desirable to determine, for instance, the maturity of a particular class of organelle sizes in a cell. For certain organelle types, less mature organelles can be smaller in size and have a shape that is not highly elongated, whereas more mature organelles can have a larger size and a shape that is more highly elongated. Therefore, by designing and making custom-shaped particle having complementarity based on known differences in average sizes and shapes of organelles, a process of separating a particular type of organelle is typically feasible. Typically, a separation or sorting process of separating does not have to be 100% efficient in order to be highly useful. In another embodiment of the current invention, specially designed custom-shaped particles are used to separate normal and diseased organelles. For example, certain diseases can lead to the formation of abnormal rod-shaped mitochondria, and it is typically feasible to design custom-shaped particles and use them in separations in order to exploit differences in shape and size of normal and abnormal biological target structures.

In another embodiment of the current invention, custom-shaped particles can be designed and produced in order to create a viable procedure for separating a fraction of a specific organelle from a lysate. For instance, we consider separating a subset of human mitochondria that are nearly spherical in shape and have a diameter that is 700 nm (see e.g. Gourley, P. L. and Naviaux, R. K. Optical phenotyping of human mitochondria in a biocavity laser. IEEE Journal of Selected Topics in Quantum Electronics, 2005, 11, 818-826). Typically, a custom-shaped particle is designed to have a surface geometry that is shape-complementary and size-complementary to at least a portion of the surface of a desired target spherical organelle. Shape-complementary custom-shaped polymeric particles of the appropriate size which contain magnetically responsive inorganic nanoparticles are fabricated and mass-produced using spatially patterned radiation (or using a variety of other lithographic methods). The lysate is mixed with the dispersion of custom-shaped polymeric particles that have been designed for a particular desired shape and size of organelle. An agent that induces the binding of the organelles to the particles is typically introduced into the mixture; this binding agent can be, for example, a depletion agent. Typically, after waiting a sufficient period of time for the aggregation to occur (which can range from seconds to days depending upon the concentrations of the organelles and particles), organelle-particle aggregates are formed. It is typically desirable for the type of aggregation to be reversible by some means, so that particles and organelles can be unbound (i.e. disaggregated) through a change in physical or chemical composition at a later stage in the process without damaging the organelles. However, if preserving or later manipulating the organelles after the separation has been achieved is desirable, then it is typically possible to use attractive interactions between the particle and organelle that lead to irreversible aggregation. Typically, following the formation of organelle-particle aggregates, an external field is applied (e.g. a magnetic field), and the particle-organelle aggregates are spatially separated from the other components of the mixture of lysate and shape-complementary particles. For instance, this can be accomplished by attaching a permanent magnet to the bottom of a vial containing the mixture so that the magnetic field gradient causes the particle-organelle aggregates to move to the bottom of the vial, and then pouring out the rest of the lysate containing organelles that are not magnetically attracted to the bottom of the vial.

In another embodiment of the current invention, once particle-organelle aggregates have been separated from the rest of the lysate, the aggregates are disaggregated by reducing the concentration of the binding agent or by removing the binding agent. Typically, for a binding agent that is a depletion agent, dilution or dialysis could be used to reduce the concentration of the depletion agent and cause the unbinding. Typically, once the disaggregation has occurred (e.g. over a time scale of seconds, but potentially as long as days), the shape-complementary particles are concentrated, isolated, and separated from the dispersion of organelles by an application of an external magnetic field. Typically, the custom-shaped particles can then be processed (e.g. washed) and re-used for subsequent separations. Typically, the dispersion of separated organelles (e.g. mitochondria having a specific size and shape) are kept in an appropriate buffer solution or serum throughout the process, and the separated organelles remain viable during the entire separation process.

Example Embodiment Demonstrating a Sorting Process

A realization of the procedure for separating target structures from non-target structures, according to a current embodiment of the current invention, is schematically illustrated in the sequence of steps shown in FIG. 5(a)-FIG. 5(h). The sequence of steps shown in FIG. 5(i)-FIG. 5(l) are also provided to illustrate an optional method of disaggregating the separated aggregates of target structures and custom-shaped particles, separating the custom-shaped particles from target structures, and re-dispersing the custom-shaped particles so that they can be re-used again in subsequent separations. It can be reasonably anticipated that, according to another embodiment of the current invention, the process can be carried out for three-dimensional shapes that have more complex surface topologies than the two-dimensional shapes that have been shown in FIG. 5 for simplicity of illustration.

According to an embodiment of the current invention, the total volume fraction of particles and structures in the fluid material are less than about 10%, and no more than 40% in order to enable re-configuration of the particles and structures.

Further Embodiments

In some embodiments of the current invention, by decorating the surfaces of the shape-complementary particles with proteins, membrane proteins, lipoproteins, lipids, peptides, polypeptides, co-polypeptides, nucleic acids, ribonucleic acids, oligomeric nucleic acids, deoxyribonucleic acids, and other biopolymers, the shape and size specificity is further enhanced by chemical selectivity of surface binding with proteins, lipids, and nucleic acids on the organelles or cells.

In some embodiments of the current invention, by repeatedly applying a separation procedure to a complex mixture that contains several different target structures using differently shaped and designed custom-shaped complementary particles, several different types of specific target structures are separated and sorted from the rest of the mixture in a rapid and massively parallel manner.

In some embodiments of the current invention, the process of sorting using custom-shaped particles can be applied to macromolecules, organelles, and larger structures such as cells.

In another embodiment of the current invention, shape-selective separations through binding and unbinding of a shape-complementary particle can also be applied to the separation of non-biological colloidal structures in a complex mixture of many different types of colloids. Typically, the ability to separate the different types is based on the ability to design a shape-complementary particle that can be selectively aggregated with one or more target biostructures and separated by applying an external field without aggregating with non-target biostructures.

In another embodiment of the current invention, the entire surface of a particle can be described as being composed of a plurality of surface regions, each of which is smaller than the particle's entire surface. Typically, the entire surface of a particle can be considered to consist of a set of surface regions. Typically, the number of surface regions into which the surface of the particle can potentially be decomposed is not unique, and this number and the shapes and sizes of the surface regions may depend upon the desired application. Typically, several different sets of surface regions could be used to describe the entire surface of the same particle. For instance, the entire surface of a cube could be imagined as consisting of six flat square-like surface regions each of which has an edge length equal to that of the cube. Alternatively, the surface of an entire cube could also be considered to be a superposition of eight corner-like surface regions; each corner-like surface region consists of an intersection of the edges of three squares, each of which has an edge length that is half of the edge length of the cube. This example shows that typically even a simple shape can be equivalently imagined as being decomposable into two or more different sets of sub-shapes; each of these sets has different numbers of surface regions having different sizes and shapes. Thus, typically, a multiplicity of different sets can potentially be used to represent the entire surface of the same particle.

In an embodiment of the current invention, the surface regions on the surface of a target particle are amenable for creating a selective attractive interaction with a complementary surface region on a custom-shaped particle, such that the selective attractive interaction (i.e. such as a selective attraction, selective bonding, selective association, selective attachment, selective sticking, or selective bonding) is selective in terms of shape, size, and/or composition of the target particle. By selective, we typically imply that the attractive interaction energy can become significantly stronger between a custom-shaped particle and a target structure (i.e. usually when the complementary surfaces of the target structure and custom-shaped particle become proximate and nearly aligned) than any attractive interaction energy between a custom-shaped particle and a non-target structure in any relative position and orientation that may be present in the same dispersion. Thus, typically, the association structure that consists of a custom-shaped particle bound to a target structure results from an attractive energy of association (i.e. bonding, binding, sticking, attraction, or attachment) between the target structure and the custom-shaped particle that is significantly stronger than the attractive interaction energy that can exist between a custom-shaped particle and any non-target structure. Typically, this bonding is at least one of: a shear-rigid attraction (e.g. van der Waals attraction between solid surfaces of the target particle and the selecting particle), a slippery attraction (e.g. induced by a depletion agent), a capillary attraction, or any other kind of attraction that has some selectivity related to the size, shape, and/or composition of a surface region on a target structure as it comes into close proximity with a surface region on a custom-shaped particle.

In some embodiments of the current invention, the attractive interaction energy between the custom-shaped particle and the target structure is significantly stronger than the energy associated with thermal fluctuations and also any other energies that might be imposed in order to ensure that non-target structures do not become bound to and aggregated with custom-shaped particles. Typically, once custom-shaped particles become bound to target structures through the attractive interaction of their mutually complementary surface regions, it is usually desirable for the attractive force between a custom-shaped particle and a target structure to remain strong enough that it strongly inhibits the separation of the target structure from the custom-shaped particle. Thus, it is typically desirable for the target structure and custom-shaped particle to remain together in as an aggregate (i.e. in an association structure) until the process of separating has been accomplished.

In some embodiments of the current invention, in order to perform the separation efficiently, it is typically desirable to empirically characterize surface regions on target structures in order to design a custom-shaped particle to have at least a portion of a surface region that is complementary in size and shape to a surface region on the target structure, which thereby would facilitate a selective attractive interaction. In addition, it is typically desirable to characterize the surface regions on non-target structures in order to design a custom-shaped particle to have surface regions that are non-complementary in order to preclude strong attractive interactions with surface regions on non-target structures. Typically, it is desirable to design a custom-shaped particle to have at least a portion of its surface that is complementary to a portion of a surface of a target structure, but wherein the shape is also designed to not have substantially complementary to any other surface regions on non-target structures, so as to provide a strong attractive interaction only between a custom-shaped particle and a target structure.

In another embodiment of the current invention, characterizing surface regions on the surfaces of target and non-target particles can be performed by many kinds of real-space imaging and reciprocal-space scattering methods. For instance, real space methods include, but are not limited to: optical microscopy, confocal optical microscopy, electron microscopy, scanning electron microscopy, transmission electron microscopy, x-ray microscopy, fluorescence imaging, dark field microscopy, cryoscopic microscopy, super-resolution microscopy, and ultramicroscopy. Real-space methods often offer more accuracy, precision, and certainty in specifying the dimensions and shapes of the surface regions on particles, since scattering methods often require the ad-hoc introduction of a model to facilitate interpretation. For instance, reciprocal-space scattering methods include but are not limited to: light scattering, dynamic light scattering, small angle light scattering, x-ray scattering, small angle x-ray scattering, dynamic x-ray scattering, neutron scattering, small angle neutron scattering, neutron reflectivity, and lensless diffraction imaging.

I claim:

1. A method of separating a mixture of discrete structures dispersed in a fluid material, comprising:

identifying a target structure from said mixture of discrete structures and a non-target structure from said mixture of discrete structures;

providing a custom-shaped particle having at least a portion of a surface that is substantially shape-complementary to a portion of a surface of said target structure;

introducing said custom-shaped particle into said fluid material;

exciting reconfigurations of said custom-shaped particle with respect to said target structure and said non-target structure;

binding said custom-shaped particle to said target structure of said custom-shaped particle through an attractive interaction to form an aggregate; and isolating said aggregate containing said target structure and said custom-shaped particle from said non-target structure, wherein said custom-shaped particle preferentially binds with said target structure without binding with said non-target structure.

2. A method of separating a mixture of discrete structures in a fluid material according to claim 1, wherein said aggregate has a binding energy associated with said attractive interaction that is sufficiently large compared with an exciting energy associated with said exciting reconfigurations so that said aggregate remains aggregated while experiencing said exciting reconfigurations.

3. A method of separating a mixture of discrete structures in a fluid material according to claim 1, wherein said exciting is at least one of thermal fluctuations, fluid flow, ultrasonic agitation, shear excitations, mixing, and compressive excitations.

4. A method of separating a mixture of discrete structures in a fluid material according to claim 1, further comprising designing said custom-shaped particle to have at least a portion of a surface that is substantially shape-complementary and size-complementary to a portion of a surface of said target structure, prior to said providing said custom-shaped particle and subsequent to said identifying said target particle.

5. A method of separating a mixture of discrete structures in a fluid material according to claim 4, wherein said designing said custom-shaped particle includes designing a surface topology of said custom-shaped particle that inhibits a binding of said custom-shaped particle to said non-target structure.

6. A method of separating a mixture of discrete structures in a fluid material according to claim 1, wherein said target structure has a maximum spatial dimension that is less than about one millimeter.

7. A method of separating a mixture of discrete structures in a fluid material according to claim 4, further comprising measuring shapes and sizes of said target structure and said non-target structure, prior to said designing and subsequent to said identifying.

8. A method of separating a mixture of discrete structures in a fluid material according to claim 1, wherein said isolating is accomplished by applying at least one of an external field, a magnetic field, an electric field, a gravitational field, a centrifugation, an ultracentrifugation, an optical field, and a fluid flow.

9. A method of separating a mixture of discrete structures in a fluid material according to claim 1, wherein said binding is created by at least one of a depletion attraction, a surface attraction, a polymer-mediated attraction, a biopolymer-mediated attraction, an electrostatic attraction, a van der Waals attraction, a hydrodynamic attraction, a magnetic attraction, and a surface charge attraction.

10. A method of separating a mixture of discrete structures in a fluid material according to claim 1, further comprising:

providing a plurality of custom-shaped particles each having at least a portion of a surface that is substantially shape-complementary to a portion of a surface of said target structure;

introducing said plurality of custom-shaped particles into said fluid material;

exciting reconfigurations of said plurality of custom-shaped particles with respect to respective target structures and respective non-target structures;

binding said plurality of custom-shaped particles to corresponding target structures through an attractive interaction to form a plurality of aggregates; and isolating said plurality of aggregates.

11. A method of separating a mixture of discrete structures in a fluid material according to claim 10, wherein a number of said plurality of custom-shaped particles is at least equal to a number of corresponding target structures in said fluid material.

12. A method of separating a mixture of discrete structures in a fluid material according to claim 1, wherein said binding is induced by adding a binding agent to said fluid material.

13. A method of separating a mixture of discrete structures in a fluid material according to claim 12, wherein said binding agent is at least one of a depletion agent, a polymer, a biopolymer, a surfactant, a nanoparticle, a nanoemulsion, a micelle, a vesicle, a microgel, an organelle, a charged colloid, and a dendrimer.

14. A method of separating a mixture of discrete structures in a fluid material according to claim 1, wherein a composition of said custom-shaped particle is magnetically responsive.

15. A method of separating a mixture of discrete structures in a fluid material according to claim 1, wherein a composition of said custom-shaped particle provides a material property which facilitates said isolating that is at least one of a density property, a magnetic property, a dielectric property, an optical property, a fluorescence property, a mechanical property, and an electromagnetic property.

16. A method of separating a mixture of discrete structures in a fluid material according to according to claim 1, wherein a plurality of said custom-shaped particles are produced using at least one of spatially patterned radiation, relief deposition templating, relief radiation templating, photolithography, ultraviolet lithography, x-ray lithography, nanoimprinting, imprinting, extrusion, stamping, templating, and dip-pen nanolithography.

17. A method of separating a mixture of discrete structures in a fluid material according to claim 1, wherein a total volume fraction of said target structures, said non-target structures, and said custom-shaped particles is less than about ten percent.

18. A method of separating a mixture of discrete structures in a fluid material according to claim 1, wherein said target structures are abnormal biological structures and said non-target structures are normal biological structures.

* * * * *